US006635240B1

(12) United States Patent
Bolich, Jr. et al.

(10) Patent No.: US 6,635,240 B1
(45) Date of Patent: Oct. 21, 2003

(54) HAIR STYLING COMPOSITIONS CONTAINING SELECT POLYALKYLENE GLYCOL STYLING AGENTS

(75) Inventors: Raymond Edward Bolich, Jr., Hillsboro, OH (US); Kenneth Wayne Rigney, Georgetown, KY (US); Alic Anthony Scott, Cincinnati, OH (US); Dennis Eugene Kuhlman, Middletown, OH (US); Michael John Schneider, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/464,172

(22) Filed: Dec. 15, 1999

Related U.S. Application Data

(63) Continuation-in-part of application No. 09/305,502, filed on May 5, 1999, now abandoned.

(51) Int. Cl.$^7$ .................... A61K 7/06; A61K 37/695; A61K 7/11; A61K 7/00; A61L 9/04
(52) U.S. Cl. ................. 424/70.1; 424/45; 424/70.12; 424/70.17; 424/401; 424/47; 514/63; 514/937; 514/941; 514/945
(58) Field of Search .................. 424/45, 401, 70.1, 424/70.12, 70.17, 47; 514/941, 937, 63, 945

(56) References Cited

U.S. PATENT DOCUMENTS

| | | | |
|---|---|---|---|
| 3,215,603 A | 11/1965 | Gross et al. .................. 167/87 |
| 3,427,382 A | 2/1969 | Haefele et al. ............... 424/71 |
| 3,876,760 A | 4/1975 | Nersesian et al. ............ 424/70 |
| 3,959,463 A | 5/1976 | Nersesian et al. ............ 424/70 |
| 4,001,392 A | 1/1977 | Curry et al. .................. 424/47 |
| 4,902,499 A | 2/1990 | Bolich, Jr. et al. ............ 424/70 |
| 4,963,348 A | * 10/1990 | Bolich et al. |
| 5,100,658 A | * 3/1992 | Bolich et al. |
| 5,211,941 A | 5/1993 | Komori et al. ................ 424/70 |
| 5,275,761 A | 1/1994 | Bergmann .................. 252/551 |
| 5,342,611 A | 8/1994 | Komori et al. ................ 424/70 |
| 5,358,667 A | 10/1994 | Bergmann .................. 252/547 |
| 5,362,484 A | 11/1994 | Wood et al. .................. 424/70 |
| 5,456,863 A | 10/1995 | Bergmann .................. 252/547 |
| 5,618,524 A | * 4/1997 | Bolich et al. |
| 5,660,190 A | 8/1997 | Tricaud et al. ............... 132/208 |
| 5,733,536 A | 3/1998 | Hill et al. ................. 424/70.12 |
| 5,750,122 A | 5/1998 | Evans et al. ................ 424/401 |
| 5,830,447 A | * 11/1998 | Hutchins et al. |
| 5,837,661 A | 11/1998 | Evans et al. ................ 510/122 |
| 5,874,092 A | 2/1999 | Roulier et al. ............... 424/401 |

FOREIGN PATENT DOCUMENTS

| | | | |
|---|---|---|---|
| EP | 268 982 | 11/1987 | ............ A61K/7/06 |
| EP | 313 307 | 10/1988 | ............ A61K/7/11 |
| EP | 566 049 | 4/1993 | ............ A61K/7/08 |
| EP | 682 935 | 5/1995 | ............ A61K/7/06 |
| EP | 240 350 | 6/1995 | ............ A61K/7/11 |
| EP | 820 758 | 7/1997 | ............ A61K/7/06 |
| EP | 0841060 | 10/1997 | |
| EP | 916 690 | 11/1998 | .............. C08J/3/03 |
| JP | 2634858 | 12/1989 | ............ A61K/9/12 |
| JP | 04290810 | 10/1992 | ............ A61K/7/00 |
| JP | 10167935 | 12/1996 | ............ A61K/7/06 |
| JP | 10-007534 | 1/1998 | ............ A61K/7/06 |
| JP | 2750807 | 2/1998 | ............ A61K/7/06 |
| JP | 10167948 | 6/1998 | ............ A61K/7/48 |
| JP | 00/204025 A2 | 7/2000 | |
| WO | 95/09599 | 4/1995 | ............ A61K/7/06 |
| WO | 97/30681 | 8/1997 | ............ A61K/7/06 |
| WO | 97/30682 | 8/1997 | ............ A61K/7/06 |
| WO | 98/38969 | 9/1998 | ............ A61K/7/00 |
| WO | WO-00/40212 A1 | 7/2000 | |
| WO | WO-00/67709 A2 | 11/2000 | |

OTHER PUBLICATIONS

*English abstracts included/attached.
**Abstract (in English).

* cited by examiner

Primary Examiner—Shelley A. Dodson
(74) Attorney, Agent, or Firm—Linda M. Sivik; Tara M. Rosnell

(57) ABSTRACT

Disclosed are hair styling compositions which comprise from about 5% to about 90% by weight of a polyalkylene glycol styling agent that is substantially free of polyalkylene glyceryl ethers, and that has a number average molecular weight of from about 190 to about 1500 and from about 5 to about 35 repeating alkylene oxide radicals wherein each of the repeating alkylene oxide radicals has from 2 to 6 carbon atoms; from about 1% to about 90% by weight of a liquid carrier which can comprise water, an organic solvent, or combinations thereof; and, optionally, from about 5% to about 40% by weight of a propellant. Also disclosed are hair styling compositions which comprise from about 5% to about 90% by weight of a polyalkylene glycol styling agent that has a number average molecular weight of from about 190 to about 1500 and from about 5 to about 35 repeating alkylene oxide radicals wherein each of the repeating alkylene oxide radicals has from 2 to 6 carbon atoms; from about 1% to about 90% by weight of a liquid carrier which can comprise water, an organic solvent, or combinations thereof; and from about 1.5% to about 60% by weight of certain silicones or silicone derivatives and, optionally, propellant.

30 Claims, No Drawings

HAIR STYLING COMPOSITIONS CONTAINING SELECT POLYALKYLENE GLYCOL STYLING AGENTS

This application is a CIP of Ser. No. 09/305,502 filed May 5, 1999 now abandoned.

FIELD OF THE INVENTION

The present invention relates to hair styling compositions which provide improved hair restyling performance. In particular, the present invention relates to hair styling compositions which contain select polyalkylene glycols that provide for improved dry hair restyling performance without reapplication of the composition and/or any additional hair styling aids.

BACKGROUND OF THE INVENTION

Hair styling compositions are well known and are commercially available in a variety of forms including mousses, gels, lotions, pumps, or hairsprays. Many of these products contain various hair styling agents to provide temporary hair styling benefits such as body, hold, luster, improved hair feel, and good style retention.

One method of providing temporary hair styling benefits from a styling product while styling the hair involves the use of a hair mousse. Many hair mousse products have been formulated such that the hair mousse composition can be applied to wet or damp hair before styling or "setting" the hair. Typically, the hair mousse compositions are aqueous formulations which contain water-soluble styling agents that provide adhesive properties to the hair while the hair is wet and being styled. These styling agents, however, can form hard breakable films on the hair as the styling process is near completion, and this can result in an unacceptable hair style or in a hair style that cannot be restyled unless additional water and/or supplemental styling products are added to the hair. Moreover, the use of aqueous hair mousse compositions which contain water-soluble styling agents can leave the hair feeling unduly sticky and stiff.

One attempt at producing an aqueous hair mousse composition that is especially effective in providing good hair styling performance without leaving the hair feeling unduly stiff or sticky involves the formulation of an aqueous hair mousse which comprises a water-soluble styling polymer, a silicone emulsion, a liquid carrier comprising a combination of water and lower alcohols, and a silicone-linear polyoxy-alkylene block copolymer surfactant which maintains stability of the silicone emulsion. Although these aqueous hair mousse compositions are effective in providing good hair styling performance and improved hair feel, they are also typically applied to wet or damp hair, and often lead to the application of an additional styling product once the hair has dried in order to achieve the desired final hairstyle form.

Another attempt at producing an aqueous aerosol hair mousse composition that provides good hair styling performance and improved hair feel involves the use of a combination of panthenol and certain low molecular weight polyalkylene glycols. The low molecular weight polyalkylene glycols, i.e., polyethylene glycols or polypropylene glycols having from 3 to about 12 ethylene glycol or propylene glycol units, help to effectively and efficiently deliver the panthenol to the hair. These hair mousse compositions, however, are also typically applied to wet or damp hair to achieve the desired hair conditioning benefits and generally require reapplication of the composition or another styling product to maintain or modify the original hairstyle.

Therefore, a need exists for hair styling compositions which provide for a desired hair style to be achieved and maintained, and which can be applied or sprayed on the hair during the styling process. A recent method of making a hair styling composition that can be applied to wet and/or dry hair during the styling process, and provide improved styling performance is described in JP 8-346608, published Jun. 23, 1998. The hair styling compositions disclosed in this publication contain polyalkylene glyceryl ethers styling agents to provide for sustained hair styling performance and improved aesthetics such as longer moisture and luster to the hair. These polyalkylene glyceryl ether styling agents typically do not readily penetrate into the hair and can remain on the hair fibers to provide the improved hair styling benefits. The polyalkylene glyceryl ether containing compositions disclosed in this particular publication, however, tend to provide minimal or no hold to the hair, and this can result in poor style achievement and poor style retention performance.

Another recent method of making a hair styling composition that can be applied during the styling process, and provide improved styling performance is described in WO 98/38969, published Sep. 11, 1998. The compositions disclosed in this publication use certain styling agents which deliver hair style performance to dry hair, and provide for the dry hair to be restyled without having to reapply the composition and without requiring the use of another styling product. The styling agents described in this reference include anionic, cationic, amphoteric, and nonionic styling polymers, preferably sulfonated anionic styling polymers which have an average molecular weight of from about 500 to about 5,000,000. These styling agents, however, have exceptional cohesive strength which provides for the hair fibers to be firmly held together, and this can cause the dry hair to feel coarse and be difficult to comb, style, and restyle.

It has now been found that other hair styling compositions, particularly aerosol hair styling compositions, can be formulated to provide improved dry hair restyle performance without the need to reapply the composition and/or add any other styling aids. Unlike the compositions described in the WO 98/38969 publication, these new aerosol hair styling compositions comprise low molecular weight, water-soluble polyalkylene glycol styling agents that are liquids or semisolids under ambient conditions and that can remain as a liquid or semisolid after the compositions have been applied and allowed to dry on the hair. These select polyalkylene glycols can provide for a fluid film to be left on the hair which can be characterized as a reformable weld that allows the hair fibers to be separated by forces such as wind, and then re-adhere using styling techniques such as combing, brushing, or running your fingers through the hair. The ability of these select polyalkylene glycol styling agents to remain as a liquid or semisolid also provides for an aerosol hair styling product that can be applied and evenly distributed onto dry hair, resulting in the dry hair feeling extremely smooth and very easy to restyle. This improved restyle performance provided by these select polyalkylene glycols can last for extended periods of several days without the need to reapply the composition and/or add any additional styling aids on the hair.

It is therefore an object of the present invention to provide aerosol or non-aerosol hair styling compositions which provide improved dry hair restyling performance and improved hair feel, and which contain select polyalkylene glycol styling agents that have a number average molecular weight of from about 190 to about 1500 and which optionally contain silicones or silicone derivatives having a molecular weight of greater than about 40,000 daltons. It is also an object of the present invention to provide an aerosol hair styling composition in the form of a hair mousse which provides improved dry hair restyling performance and improved hair feel, and which contains select polyalkylene glycol styling agents that have a number average molecular weight of from about 190 to about 1500 and which optionally contain silicones or silicone derivatives having a molecular weight of greater than about 40,000 daltons. It is yet another object of the present invention to provide an aerosol hair styling composition which provides improved dry hair restyling performance and improved hair feel for extended periods of time without the need to reapply the composition or add any other styling aids. It is still yet another object of the present invention to provide an aerosol hair styling composition that is a leave-on hair styling composition, and further to provide such a composition that does not feel unduly sticky or stiff after the composition has been applied and allowed to dry on the hair.

SUMMARY OF THE INVENTION

The present invention is directed to aerosol hair styling compositions which comprise (a) from about 5% to about 90% by weight of a water-soluble polyalkylene glycol that is substantially free of polyalkylene glyceryl ethers and that has a number average molecular weight of from about 190 to about 1500 and from about 5 to about 35 repeating alkylene oxide radicals wherein each of the repeating alkylene oxide radicals has from 2 to 6 carbon atoms; (b) from about 1% to about 90% by weight of a liquid carrier; and (c) from about 5% to about 40% by weight of a propellant.

The present invention is also directed to hair mousse compositions which comprise (a) from about 5% to about 25% by weight of a water-soluble polyalkylene glycol that is substantially free of polyalkylene glyceryl ethers and that has a number average molecular weight of from about 190 to about 1500 and from about 5 to about 35 repeating alkylene oxide radicals wherein each of the repeating alkylene oxide radicals has from 2 to 6 carbon atoms; (b) from about 10% to about 90% by weight of water; and (c) from about 5% to about 40% by weight of a propellant. The present invention is also directed to a method of making such a hair mousse composition.

The present invention is also directed to hair styling compositions which comprise (a) from about 65% to about 99% by weight of a water-soluble polyalkylene glycol that is substantially free of polyalkylene glyceryl ethers and that has a number average molecular weight of from about 190 to about 1500 and from about 5 to about 35 repeating alkylene oxide radicals wherein each of the repeating alkylene oxide radicals has from 2 to 6 carbon atoms; and (b) from about 1% to about 30% by weight of a liquid carrier.

The present invention is also directed to hair styling compositions which comprise (a) from about 2% to about 80% by weight of a water-soluble polyalkylene glycol that has a number average molecular weight of from about 900 to about 1500 and from about 5 to about 35 repeating alkylene oxide radicals, wherein each of the repeating alkylene oxide radicals has from 2 to 6 carbon atoms, (b) from about 1.5% to about 60% of a silicone or silicone derivative having a molecular weight of greater than about 40,000, and (c) from about 1% to about 90% of a liquid carrier, wherein the ratio of the polyalkyene glycol to silicone or silicone derivative ranges from about 1:4 to about 4:1.

It has been found that the aerosol hair styling compositions of the present invention can provide improved dry hair restyling performance for several days without the need to reapply the composition or add any other styling aid on the hair. This is accomplished by formulating an aerosol hair styling composition, especially a hair mousse, that contains select polyalkylene glycol styling agents which are capable of being deposited on the hair as a liquid or semisolid and can remain a liquid or semisolid after the composition has been allowed to dry on the hair. These select styling agents can create a fluid film on the hair in the form of a reformable weld that provides for improved hair restyling performance such as 1) dry hair styled and restyled without reapplication of the compositions and/or water and/or any other styling aid, 2) dry hair restyled for several days by simply combing or brushing the hair, and 3) improved styling aesthetics including frizz and volume control, superior hair hold, and superior hair feel.

DETAILED DESCRIPTION OF THE INVENTION

The hair styling compositions of the present invention comprise select water-soluble polyalkylene glycols that can be deposited on the hair and form reformable welds on the hair fibers. These compositions are intended for application to dry hair, and are preferably formulated as leave-on aerosol hair styling products.

The term "leave-on" as used herein refers to compositions that contain ingredients that are intended to be deposited and left on the hair for extended periods (e.g., several hours or days) until the ingredients are subsequently removed by water and/or by shampooing the hair.

The term "reformable weld" as used herein refers to residues which are left on dry hair and which contain materials that are liquid or semisolid at ambient condition, and that can remain as a liquid or semisolid after the compositions described herein have been applied and allowed to dry on the hair.

The term "ambient conditions" as used herein refers to surrounding conditions at about one atmosphere of pressure, at about 50% relative humidity, and at about 25° C.

The term "substantially free" as used herein, unless otherwise specified, refers to preferred negative limitations of some embodiments of the compositions of the present invention, and are directed to the amount and concentration of polyalkylene glyceryl ether styling agents, or derivatives thereof, in the compositions. The term "substantially free" means that the compositions preferably contain less than an effective amount of such agents when used alone to provide any hair styling performance when the compositions are applied to the hair. In this context, the negative limitations pertain only to those polyalkylene glyceryl ether styling agents which are also a liquid or semisolid under ambient conditions, and which are not silicone-containing materials. Generally, the compositions preferably contain less than 5%, more preferably less than 2%, even more preferably less than 1%, most preferably zero percent, of such agents by weight of the compositions.

The hair styling compositions of the present invention can comprise, consist of, or consist essentially of the essential elements and limitations of the invention described herein, as well as any of the additional or optional ingredients, components, or limitations described herein.

All percentages, parts and ratios are by weight of the total composition, unless otherwise specified. All such weights as they pertain to listed ingredients are based on the active level and, therefore, do not include solvents or by-products that may be included in commercially available materials, unless otherwise specified.

Styling Agent

The hair styling compositions of the present invention comprise a water-soluble liquid or semisolid hair styling agent suitable for being left on dry hair as a liquid or semisolid after the composition has been applied and allowed to dry on the hair. These hair styling agents provide for a fluid film to be left on the hair which can be characterized as a reformable weld that provides dry hair restyling performance without the need to reapply the compositions or add additional styling aids on the hair.

The concentration of the styling agent may vary with each selected hair styling formulation, but such concentrations will generally range from about 1% to about 90%, preferably from about 3% to about 75%, more preferably from about 7.5% to about 50%, even more preferably from about 10% to about 25%, by weight of the composition. For aerosol hair styling compositions in the form of a mousse product, the concentration of the styling agent preferably range from about 5% to about 25%, more preferably from about 7.5% to about 25%, even more preferably from about 10% to about 20%, by weight of the composition. For hair styling compositions which contain a silicone or silicone derivative, the concentration of the styling agent preferably ranges from about 2% to about 80%, more preferably from about 3% to about 75%, most preferably from about 4% to about 70% by weight of the composition.

Suitable styling agents for use in the hair styling compositions of the present invention include any known or otherwise effective hair styling agents that are liquids or semisolids under ambient conditions and that can remain a liquid or semisolid after the composition has been applied and allowed to dry on dry hair, except that polyalkyline glycerol ethers should not be employed in the compositions herein, unless the composition contains a silicone oil or silicone emulsion. It has been found that certain liquid or semisolid styling agents, particularly low molecular weight polyalkylene glycols, can leave a fluid film on the hair that allows the hair fibers to be separated by forces such as wind, and then re-adhere using styling techniques such as combing, brushing, or running your fingers through the hair. This separation/readherence property provided by the styling agents defined herein results in improved dry hair restyling performance for several days without leaving the hair feeling unduly sticky or stiff, and without having to reapply the compositions described herein and/or add any other additional styling aids on the hair.

Nonlimiting examples of styling agents suitable for use in the aerosol hair styling compositions of the present invention include water-soluble materials such as polyalkylene glycols, polyethylene/polypropylene glycol copolymers, polyethylene/polypropylene diol copolymers, polyglycerins, and mixtures thereof, and/or their derivatives, and/or mixtures thereof, excluding the water-soluble polyalkylene glyceryl ethers which are also liquids or semisolids under ambient conditions, except in embodiments wherein the styling composition contains a silicone or silicone derivative, in which case such water-soluble polyalkylene glycol ethers may desirably be included. In this context, "water-soluble" refers to those styling materials that have a solubility in water at 25° C. of greater than 0.6%, preferably greater than 1.0%, more preferably greater than about 1.5% by weight.

Preferred styling agents suitable for use herein include those water-soluble polyalkylene glycols which conform to the formula:

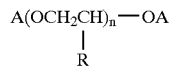

wherein A is selected from the group consisting of methyl or hydrogen or mixture thereof and wherein R is selected from the group consisting of H, methyl, and mixtures thereof. When R is H, these materials are polymers of ethylene oxide, which are also known as polyethylene oxides, polyoxyethylenes, and polyethylene glycols. When R is methyl, these materials are polymers of propylene oxide, which are also known as polypropylene oxides, polyoxypropylenes, and polypropylene glycols. When R is methyl, it is also understood that various positional isomers of the resulting polymers can exist.

In the above structure, n has an average value of from 4 to about 35, preferably from about 5 to about 35, more preferably from about 5 to about 30, and even more preferably from about 5 to about 20.

Specific examples of preferred polyalkylene glycol polymers include polyethylene/polypropylene glycol copolymers (e.g., methoxy, ethoxy, propoxy, butoxy, and pentoxy, polyethylene/polypropylene glycols), triglycerin, hexaglycerin, PEG-4, PEG-6, PEG-5, PEG-6, PEG-8, PEG-12, PEG-14, PEG-18, PEG-20, PEG-32, and mixtures thereof. Most preferred are those polyalkylene glycols which have a number average molecular weight of from about 190 to about 1500, preferably from about 300 to about 1200, more preferably from about 400 to about 1000; and from about 5 to about 35, preferably from about 5 to about 30, more preferably from about 5 to about 20, repeating alkylene oxide radicals wherein each of the repeating alkylene oxide radicals has from 2 to 6 carbon atoms. Specific examples of the most preferred polyalkylene glycols include, but are not limited to, PEG-4 wherein R equals methyl and n has an average value of about 4; PEG-8 wherein R equals H and n has an average value of about 8 (PEG-8 is also known as Carbowax 400, which is available from Union Carbide); PEG-12 wherein R equals H and n has an average value of about 12 (PEG-12 is also known as Carbowax 600, which is available from Union Carbide); and PEG-20 wherein R equals H and n has an average value of about 20 (PEG-20 is also known as Carbowax 900, which is available from Union Carbide).

In addition to the styling agent, the hereinbefore described hair styling compositions of the present invention may further comprise one or more optional styling polymers which can help provide improved initial hair hold performance. The total concentration of such optional styling polymers ranges from about 0.25% to about 5%, preferably from about 0.5% to about 4.0%, by weight of the compositions.

Optional styling polymers for use in combination with the styling agent defined herein include any known or otherwise effective styling polymer, provided that the optional styling polymer is soluble in the liquid carrier described herein which contains the optional styling polymer and styling agent, and provided that under test conditions of 27° C. and 15% relative humidity the optional styling polymer is insoluble in the residue described herein and can form a solid film that is surrounded by the styling agent material after evaporation of the liquid carrier and any other volatile materials contained in the aerosol hair styling compositions of the present invention. Such optional styling polymers include, but are not limited to, polysaccharide styling polymers. Specific nonlimiting examples of suitable polysaccharide styling polymers include anionic polysaccharides, cationic polysaccharides, and glucosamine polysaccharide derivatives. The glucosamine polysaccharide derivatives are the preferred optional styling polymers.

Suitable optional cationic polysaccharide styling polymers for use herein include, but are not limited to, copolymers of hydroxyethylcellulose and diallyidimethyl ammonium chloride (referred to in the industry by CTFA as Polyquaternium-4) such as those commercially available from National Starch (Bridgewater, New Jersey) under the CELQUAT tradename (e.g., CELQUAT L-200 and CELQUAT H-100); and cationic quaternary ammonium-containing polymers, including, for example, homopolymers of hydroxyethyl cellulose reacted with a trimethyl ammonium substituted epoxide, (referred to in the industry by CTFA as Polyquaternium-10) such as those commercially available from Amerchol Corp. (Edison, N.J.) under the UCARE tradename (e.g. UCARE POLYMER JR-400, and UCARE POLYMER LR-400), and those commercially available from National Starch (Bridgewater, N.J.) under the CELQUAT tradename (e.g., CELQUAT SC 230 and CELQUAT SC 240).

Also useful are the nonionic cellulosic derivatives, such as methyl and hydroxyalkyl celluloses. More specifically, the hydroxyethyl celluloses, sold under various tradenames (e.g., Natrosol by Aqualon, and Cellosize by Union Carbide) are available in a wide variety of molecular weights and degrees of substitution. Methyl celluloses are available from Dow Chemical Company and hydroxypropyl methylcellulose is available from Aqualon. Examples of materials as Klucel H, Natrosol 300H, and Cellosize QP-40.

When the optional styling polymers are used, blends of cationic and nonionic cellulose derivatives wherein the cationic polysaccharide comprises from about 15% to about 85%, preferably from about 20% to about 70%, more preferably from about 25% to about 50% of the blend are preferred. An especially preferred blend is CELQUAT 1-2000 and Natrosol 250 JR wherein the CELQUAT comprises from about 15% to about 85% of the blend.

Other optional polysaccharide styling polymers for use in combination with the styling agent in the aerosol hair styling compositions of the present invention include those polysaccharide styling polymers which are derived from chitin, a glucosamine polysaccharide that is extracted from the shells of crabs, lobsters, and the like. An example of the use of chitin to make a chitin derivative for use in the compositions herein is the preparation of Chitosan, a water-soluble chitin derivative that is prepared by the known process of deacylation of the chitin compound. The chitin derivatives can also be prepared by other methods well known in the art for the preparation of such materials, including the hydroxypropylation of the chitin compound. The chitin derivatives suitable for use as an optional styling polymer herein include those chitin derivatives which are commercially available in a neutralized or unneutralized form. In the event that a neutralized chitin derivative is used, suitable neutralizing agents include, but are not limited to, lactic acid, pyrrolidone carboxylic acid, and glycolic acid.

Specific examples of preferred chitin derivatives for use as an optional styling polymer include, but are not limited to, Kytamer L and Kytamer PC ( both are neutralized Chitosan materials commercially available from the Amerchol Corp., located in Edison, N.J.); and Hydagen HCMF molecular weight (MW) of 50,000 to 1,000,000, Hydagen DCMF MW of 300,000 to 2,000,000, and Hydagen CMFP MW of 500,000 to 5,000,000 ( all are unneutralized Chitosan materials commercially available from the Henkel Corp., located in Hoboken, N.J.). Kytamer L is the most preferred chitin derivative.

The hair styling compositions of the present invention can also be formulated as nonaerosol hair styling compositions which are suitable for topical application to the hair or skin. For nonaerosol hair styling product forms such as pomades, the concentration of the styling agent preferably ranges from about 65% to about 99%, more preferably from about 65% to about 95%, even more preferably from about 65% to about 90%, by weight of the composition. Pomades may further comprise combinations of the styling agent and optional styling polymers described herein, and any of the other optional ingredients described herein.

Liquid Carrier

The hair styling compositions of the present invention comprise any known or otherwise effective liquid carrier that is suitable for use in formulations intended for topical application to human hair or skin. The liquid carrier helps to solubilize or disperse the styling agents described hereinbefore. The liquid carrier can comprise one or more liquid carriers provided that the selected styling agent is sufficiently miscible or dispersible in the selected liquid carrier. The liquid carrier described herein is also suitable for use in the nonaerosol hair styling compositions of the present invention.

The total concentration of the liquid carrier in the composition will vary with the type of liquid carrier selected, the type of styling agent used in combination with the liquid carrier, and the solubility of the selected styling agent in the selected liquid carrier, and so forth. Preferred total concentration of the liquid carrier ranges from about 1% to about 90%, preferably from about 3% to about 90%, more preferably from about 5% to about 85%, by weight of the composition.

Suitable liquid carriers for use in the hair styling compositions of the present invention include volatile liquid carrier materials. In this context, the term "volatile" refers to materials which have a boiling point of less than about 260° C., preferably from about 50° C. to about 260° C., more preferably from about 60° C. to about 200° C. (at about one atmosphere of pressure).

Nonlimiting examples of volatile liquid carriers include water; organic solvents such as $C_1$–$C_6$ alkanols, carbitol, and acetone; and combinations thereof. Specific examples of suitable $C_1$–$C_6$ alkanols include, but are not limited to, ethanol, n-propanol, isopropanol, n-butanol, amyl alcohol, and mixtures thereof. Preferred $C_1$–$C_6$ alkanols include $C_2$–$C_4$ monohydric alcohols such as ethanol, isopropanol, and mixtures thereof.

In the event that the hair styling compositions of the present invention comprise combinations of water and an organic solvent such as $C_1$–$C_6$ alkanols, water is preferably included at concentrations of from about 40% to about 90%, more preferably from about 50% to about 90%, even more preferably from about 60% to about 90%; and the $C_1$–$C_6$ alkanols are preferably included at total concentrations of from about 1% to about 15%, more preferably from about 3% to about 15%, even more preferably from about 5% to about 10%, by weight of the composition.

Optional Components

A. Silicone

Also optionally present in the compositions herein is a non-volatile silicone or silicone derivative. When present, the silicone or silicone derivative is typically present in the composition herein at a level of from about 1.5% to about 60%, preferably from about 2.0% to about 20%, more preferably from about 2% to about 10%, by weight of the compositions. For compositions which contain a silicone or silicone derivative, the ratio of polyoxyalkylene glycol to silicone or silicone derivative must range from about 4 to 1 to 1 to 4, preferably from about 3 to 1 to 1 to 3. If the ratio of the polyalkylene glycol to silicone or silicone derivative is less than about 4:1, hair treated with the hair styling composition may appear less glossy and the feel of the hair may become undesirable. On the other hand, if the ratio of the polyalkylene glycol to silicone or silicone derivative is greater than about 1:4, hair treated with the styling composition may appear frizzy.

The silicones or silicone derivatives optionally incorporated into the styling compositions herein have a molecular weight of greater than about 40,000, preferably greater than about 60,000, more preferably greater than about 80,000.

The silicone may be added to the product in any form. For example, it may be added to the propellant (in the case of aerosol products) or it may be added to the product as a neat fluid or as a pre-formed emulsion. When the silicone or silicone derivative is added to the composition as a pre-formed emulsion, the surfactant content (weight percent) in the emulsion should not exceed 25% of the silicone content of the emulsion or an undesirable hair feel could result. Because polymerization emulsions tend to require a lot of surfactant in order to form the emulsion, it is preferred that if pre-formed emulsions are used that they be mechanical emulsions.

Non-limiting examples of nonvolatile silicones include nonvolatile soluble silicones, nonvolatile insoluble silicones, or combinations thereof. In this context, the term "soluble" means that the silicone is miscible with the liquid carrier so as to form part of the same phase. Conversely, the term "insoluble" means that the silicone forms a separate, discontinuous phase from the liquid carrier, such as in the form of an emulsion, microemulsion, or a suspension of droplets of the silicone. The term "nonvolatile" as used in this context means that the silicone has a boiling point of at least about 265° C., preferably at least about 275° C., more preferably at least about 300° C. Such materials exhibit very low or no significant vapor pressure at ambient conditions.

Suitable nonvolatile insoluble silicones include those insoluble silicone fluids such as polyalkylsiloxanes, polyarylsiloxanes, polyalkylaryl siloxanes, polyether siloxane copolymers, and mixtures thereof. Other nonvolatile insoluble silicone fluids having feel enhancing properties can also be used. In this context, the term "silicone fluid" refers to those silicone materials which have a M.W. of greater than about 40,000.°

Nonlimiting examples of silicone fluids for use in the aerosol hair styling compositions of the present invention include polyalkyl or polyaryl siloxanes which conform to the formula:

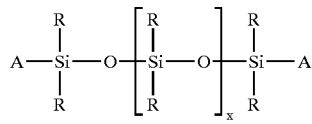

wherein R is alkyl or aryl, and x is an integer from about 7 to about 8,000. "A" represents groups which block the ends of the silicone chains.

The alkyl or aryl groups substituted on the siloxane chain (R) or at the ends of the siloxane chains (A) may have any structure as long as the resulting silicones remain fluid at ambient conditions, are hydrophobic, are neither irritating, toxic nor otherwise harmful when applied to the hair or skin, are compatible with the other components of the composition, are chemically stable under normal use and storage conditions, and are capable of being deposited on and of improving the feel of hair or skin.

Suitable A groups include methyl, ethyl, phenyl, phenylene, hydroxy, methoxy, ethoxy, propoxy, and aryloxy. The two R groups on the silicone atom may represent the same group or different groups. Preferably, the two R groups represent the same group. Suitable R groups include methyl, ethyl, propyl, phenyl, phenethyl,methylphenyl and phenylmethyl. The preferred silicone fluids are polydimethylsiloxane, polydiethylsiloxane, and polymethylphenylsiloxane. Polydimethylsiloxane is most preferred.

Specific examples of nonvolatile insoluble silicone fluids include, but are not limited to, polydimethylsiloxanes such as the Viscasil R® and SF96200 series (commercially available from the General Electric Co.), and the Dow Coming 200® series (commercially available from Dow Coming Corp.); polymethylphenylsiloxane such as SF1075® methyl phenyl fluid (commercially available from the General Electric Co).

Pre-emulsified silicones are especially useful as they can usually be directly added to the batch without high shear mixing equipment. Examples of preferred silicone emulsions are SM2169 and SM2140 from General Electric, D.C 1664 offered by Dow Coming, BY22-029 offered by Toray, and KM902 offered by Shin-Etsu.

Other suitable silicone fluids are disclosed in U.S. Pat. No. 2,826,551, issued to Geen; U.S. Pat. No. 3,964,500, issued to Drakoff, on Jun. 22, 1976; U.S. Pat. No. 4,364,837, issued to Pader; and British Patent 849,433, issued to Woolston, all of which disclosures are incorporated herein by reference.

Other suitable silicones include insoluble silicone gum. The term "silicone gum", as used herein, means polyorganosiloxane materials having a viscosity at 25° C. of greater than or equal to 1,000,000 centistokes. Silicone gums are described by Petrarch and others including U.S. Pat. No. 4,152,416, Spitzer et al., issued May 1, 1979; and Noll, Walter, Chemistry and Technology of Silicones, New York: Academic Press 1968. The "silicone gums" will typically have a mass molecular weight in excess of about 200,000, generally between about 200,000 and about 1,000,000. Specific examples include polydimethylsiloxane, (polydimethylsiloxane) (methylvinysiloxane)copolymer, poly(dimethylsiloxane)(diphenysiloxane) (methylvinysiloxane)cop olymer, and mixtures thereof.

Other suitable silicones include a silicone resin. Silicone resins are highly crosslinked polymeric siloxane systems. The crosslinking is introduced through the incorporation of trifunctional and tetrafunctional silanes with monofunctional or difunctional, or both, silanes during manufacture of the silicone resin. As is well understood in the art, the degree of crosslinking that is required in order to result in a silicone resin will vary according to the specific silane units incorporated into the silicone resin. In general, silicone materials which have a sufficient level of trifunctional and tetrafunctional siloxane monomer units (and hence, a sufficient level of crosslinking) such that they dry down to a rigid, or hard, film are considered to be silicone resins. The ratio of oxygen atoms to silicon atoms is indicative of the level of crosslinking in a particular silicone material. Silicone materials which have at least about 1.1 oxygen atoms per silicon atom will generally be silicone resins herein. Preferably, the ratio of oxygen:silicon atoms is at least about 1.2:1.0. Silanes used in the manufacture of silicone resins include monomethyl-, dimethyl-, trimethyl-, monophenyl-, diphenyl-, methylphenyl-, monovinyl-, and methylvinyl-chlorosilanes, and tetrachlorosilane, with the methyl-substituted silanes being most commonly utilized. Preferred resins are offered by General Electric as GE SS4230200 and SS4267®. Commercially available silicone resins will generally be supplied in a dissolved form in a low viscosity volatile or nonvolatile silicone fluid. The silicone resins for use herein should be supplied and incorporated into the present compositions in such dissolved form, as will be readily apparent to those skilled in the art.

Background material on silicones including sections discussing silicone fluids, gums, and resins, as well as manufacture of silicones, can be found in Encyclopedia of Polymer Science and Engineering, Volume 15, Second Edition, pp. 204–308, John Wiley & Sons, Inc., 1989, incorporated herein by reference.

B. Propellant

The aerosol hair styling compositions of the present invention comprise a propellant suitable for aerosol delivery of the composition to the desired application surface. The total concentration of the propellant in the aerosol hair styling composition can include one or more propellants, the total propellant concentration typically ranging from about 5% to about 40%, preferably from about 5% to about 25%, more preferably from about 5% to about 15%, by weight of the composition.

Nonlimiting examples of suitable propellants include hydrocarbons, nitrogen, carbon dioxide, nitrous oxide, atmospheric gas, 1,2-difluoroethane (Hydrofluorocarbon 152A) supplied as Dymel 152A by Dupont, dimethylether, and mixtures thereof Preferred are the hydrocarbon propellants, specific examples of which include propane, butane, and isobutane. Most preferred is a hydrocarbon propellant containing a mixture of propane and isobutane, specific examples of which include Aeron A-46 and Aeron A-70 (both are commercially available from Diversified CPC).

C. Other Optional Components

In addition to the essential components described hereinbefore, the hair styling compositions of the present invention may further comprise one or more optional components known or otherwise effective for use in hair care or personal care products, provided that the optional components are physically and chemically compatible with the essential components described herein, or do not otherwise unduly impair product stability, aesthetics, or performance. Nonlimiting examples of such optional components are disclosed in International Cosmetic Ingredient Dictionary, Fifth Edition, 1993, and CTFA Cosmetic Ingredient Handbook, Second Edition, 1992, both of which are incorporated by reference herein in their entirety. Some nonlimiting examples of such optional components are disclosed below.

Optional Gelling Agent

The hair styling compositions of the present invention preferably further comprise a gelling agent to help provide the desired viscosity to the residue which remains on the hair after the composition has been applied and allowed to dry on the hair. The preferred optional gelling agent also helps to provide for improved hair hold performance. Suitable optional gelling agents include any material known or otherwise effective in providing any gelling or measurable viscosity increase to the residue. The concentrations of the optional gelling agent in the compositions range from about 0.1% to about 10%, preferably from about 0.2% to about 5.0%, by weight of the compositions.

Nonlimiting examples of suitable optional gelling agents include crosslinked carboxylic acid polymers; unneutralized crosslinked carboxylic acid polymers; unneutralized modified crosslinked carboxylic acid polymers; crosslinked ethylene/maleic anhydride copolymers; unneutralized crosslinked ethylene/maleic anhydride copolymers (e.g., EMA 81 commercially available from Monsanto); unneutralized crosslinked allyl ether/acrylate copolymers (e.g., Salcare SC90 commercially available from Allied Colloids); unneutralized crosslinked copolymers of sodium polyacrylate, mineral oil, and PEG-1 trideceth-6 (e.g., Salcare SC91 commercially available from Allied Colloids); unneutralized crosslinked copolymers of methyl vinyl ether and maleic anhydride (e.g., Stabileze QM-PVM/MA copolymer commercially available from International Specialty Products); hydrophobically modified nonionic cellulose polymers; hydrophobically modified ethoxylate urethane polymers (e.g., Ucare Polyphobe Series of alkali swellable polymers commercially available from Union Carbide); and combinations thereof. In this context, the term "unneutralized" means that the optional polymer and copolymer gelling agent materials contain unneutralized acid monomers.

Preferred optional gelling agents include water-soluble unneutralized crosslinked ethylene/maleic anhydride copolymers, water-soluble unneutralized crosslinked carboxylic acid polymers, and water-soluble hydrophobically modified nonionic cellulose polymers. The crosslinked carboxylic acid polymers and hydrophobically modified nonionic cellulose polymers are described in detail hereinbelow.

Carboxylic Acid Polymers

The optional carboxylic acid polymers suitable for use herein are those crosslinked compounds containing one or more monomers derived from acrylic acid, substituted acrylic acids, esters of acrylic acid, esters of substituted acrylic acids, corresponding salts thereof, and combinations thereof, wherein the crosslinking agent contains two or more carbon-carbon double bonds and is derived from a polyhydric alcohol. Specific examples of these carboxylic acid polymers include crosslinked carboxylic acid homopolymers and crosslinked carboxylic acid copolymers. Combinations of these two types of polymers are also useful herein.

The term "substituted" as used herein refers to chemical moieties known or otherwise effective for attachment to gelling agents or other compounds. Such substituents include those listed and described in C. Hansch and A. Leo, *Substituent Constants for Correlation Analysis in Chemistry and Biology* (1979), which listing and description are incorporated herein by reference. Examples of such substituents include, but are not limited to, alkyl, alkenyl, alkoxy, hydroxy, oxo, nitro, amino, aminoalkyl (e.g., aminomethyl, etc.), cyano, halo, carboxy, alkoxyaceyl (e.g., carboethoxy, etc.), thiol, aryl, cycloalkyl, heteroaryl, heterocycloalkyl (e.g., piperidinyl, morpholinyl, pyrrolidinyl, etc.), imino, thioxo, hydroxyalkyl, aryloxy, arylalkyl, and combinations thereof.

The term "corresponding salts" as used herein refers to cationic salts formed at any acidic (e.g., carboxyl) group, or anionic salts formed at any basic (e.g., amino) group, either of which are suitable for topical application to human skin. Many such salts are known in the art, examples of which are described in World Patent Publication 87/05297, Johnston et al., published September 11, 1987, which description is incorporated herein by reference.

Preferred optional crosslinked carboxylic acid polymers are those crosslinked carboxylic acid homopolymers or copolymers which contain unneutralized acid monomers. It has been found that crosslinked carboxylic acid polymers which have unneutralized acid monomers are especially effective in providing gelling properties to the residue without suppressing the ease of removability of the residue by shampooing the hair.

Partially or fully neutralized crosslinked carboxylic acid polymers are also suitable for use as an optional gelling agent in the hair styling compositions of the present invention, provided that these carboxylic acid polymers are included in combination with one or more styling agents which have an average solubility parameter of above about 14 $(cal/cm^3)^{0.5}$ to about 20 $(cal/cm^3)^{0.5}$. Solubility parameters for the styling agents or other materials, and means for determining such parameters, are well known in the chemical arts. A description of solubility parameters and means for determining them are described by C.D. Vaughan, "Solubility Effects in Product, Package, Penetration and Preservation" 103 Cosmetics and Toiletries 47–69, October 1988; and C. D. Vaughan, "Using Solubility Parameters in Cosmetics Formulation", 36 J. Soc. Cosmetic Chemists 319–333, September/October, 1988, which descriptions are incorporated herein by reference.

Suitable crosslinked carboxylic acid homopolymers include those crosslinked homopolymers which have an acrylic acid monomer, or derivative thereof, (e.g., wherein the acrylic acid has substituents on the two and three carbon positions independently selected from the group consisting of $C_{1-4}$ alkyl, —CN, —COOH, and mixtures thereof). Preferred monomers include acrylic acid, methacrylic acid, ethacrylic acid, and mixtures thereof, with acrylic acid being the most preferred.

Suitable crosslinked carboxylic acid copolymers include those crosslinked copolymers which have a first monomer selected from the group consisting of an acrylic acid or derivative thereof as defined above, a short chain alcohol (i.e., a $C_{1-4}$) acrylate ester monomer or derivative thereof (e.g., wherein the acrylic acid portion of the ester has substituents on the two and three carbon positions independently selected from the group consisting of $C_{1-4}$ alkyl, —CN, —COOH, and mixtures thereof), and mixtures thereof; and a second monomer which is a long chain alcohol (i.e. $C_{8-40}$) acrylate ester monomer or derivative thereof (e.g., wherein the acrylic acid portion of the ester has substituents on the two and three carbon positions independently selected from the group consisting of $C_{1-4}$ alkyl, —CN, —COOH, and mixtures thereof). Preferred first monomers include acrylic acid, methacrylic acid, and ethacrylic acid, $C_{1-4}$ alcohol acrylate esters, $C_{1-4}$ alcohol methacrylate esters, $C_{1-4}$ alcohol ethacrylate esters, and mixtures thereof, with acrylic acid, methacrylic acid, $C_{1-4}$ alcohol acrylate esters, $C_{1-4}$ alcohol methacrylate esters, and mixtures thereof being the most preferred. Preferred second monomers include $C_{8-40}$ alkyl acrylate esters, with $C_{10-30}$ alkyl acrylate esters being the most preferred. In other words, the preferred crosslinked carboxylic acid copolymers include those copolymers which have a first monomer selected from the group consisting of acrylic acid, methacrylic acid, $C_{1-4}$ alcohol acrylate esters, $C_{1-4}$ alcohol methacrylate esters, and mixtures thereof, and a $C_{10-30}$ alkyl acrylate ester second monomer.

The crosslinking agent in both of these types of polymers is a polyalkenyl polyether of a polyhydric alcohol containing more than one alkenyl ether group per molecule, wherein the parent polyhydric alcohol contains at least 3 carbon atoms and at least 3 hydroxyl groups. Preferred crosslinking agents are those selected from the group consisting of allyl ethers of sucrose, allyl ethers of pentaerythritol, and mixtures thereof.

Examples of commercially available crosslinked carboxylic acid homopolymers suitable for use herein include the carbomers, which are homopolymers of acrylic acid crosslinked with allyl ethers of sucrose or pentaerytritol. The carbomers are available as the Carbopol® 900 series from B.F. Goodrich. Most preferred are the commercially available carbomers which have unneutralized acid monomers.

Examples of commercially available crosslinked carboxylic acid copolymers suitable for use herein include copolymers of $C_{10-30}$ alkyl acrylates with one or more monomers of acrylic acid, methacrylic acid, or one of their short chain (i.e. $C_{1-4}$ alcohol) esters, wherein the crosslinking agent is an allyl ether of sucrose or pentaerytritol. These copolymers are known as acrylates/C10–30 alkyl acrylate crosspolymers and are commercially available as Carbopol® 1342, Pemulen TR-1, and Pemulen TR-2, from B.F. Goodrich.

Suitable crosslinked carboxylic acid polymers are more fully described in U.S. Pat. No. 5,087,445, to Haffey et al., issued Feb. 11, 1992; U.S. Pat. No. 4,509,949, to Huang et al., issued Apr. 5, 1985; U.S. Pat. No. 2,798,053, to Brown, issued Jul. 2, 1957; which descriptions are incorporated by reference herein. See also, *CTFA International Cosmetic Ingredient Dictionary*, fourth edition, 1991, pp. 12 and 80; which description is also incorporated herein by reference.

Modified Nonionic Cellulose Polymers

The preferred optional gelling agent suitable for use in the aerosol hair styling compositions of the present invention also include water-soluble hydrophobically modified nonionic cellulose polymers. The term "water-soluble hydrophobically modified nonionic polymers" refers to those water-soluble nonionic polymers which have been modified to comprise substituted hydrophobic groups to make the polymer less soluble in water. Hence, the nonionic cellulose polymers comprise a water-soluble cellulosic chain (or hydrophilic cellulosic chain) which forms the backbone, wherein the backbone comprise substituted hydrophobic groups. Suitable substituted hydrophobic groups include C8–C22 alkyl, arylalkyl, alkylaryl groups, and mixtures thereof. The degree of substitution on the backbone should be from about 0.10% to about 1.0%, depending on the particular polymer backbone. The nonionic cellulose polymers generally contain a ratio of hydrophilic substituents to hydrophobic substituents of from about 10:1 to about 1000:1.

Nonlimiting examples of preferred hydrophobically modified nonionic cellulose polymers include those nonionic cellulose polymers which comprise a cellulose ether substrate and a long chain alkyl modifier. In this context, the term "long chain alkyl modifier" means that the modifying compound can comprise an alkyl radical or other functional groups such as an alphahydroxyalkyl radical, a urethane radical, or an acyl radical. These polymers, and methods of making the polymers, are also described in U.S. Pat. No. 4,228,277, issued to Landoll on Oct. 14, 1980, which description is incorporated herein by reference.

Suitable cellulose ether substrates include any known or otherwise effective water-soluble nonionic cellulose ether. Nonlimiting examples of suitable water-soluble nonionic cellulose ethers include, but are not limited to, hydroxyethyl cellulose, hydroxypropyl cellulose, methyl cellulose, hydroxypropyl methyl cellulose, ethyl hydroxyethyl cellulose, and methyl hydroxyethyl cellulose. The amount of the nonionic substituent (e.g., methyl, hydroxyethyl, or hydroxypropyl substituent) is not critical provided that the amount is sufficient to assure that the ether is water-soluble.

The preferred cellulose ether substrate is hydroxyethyl cellulose (HEC) which has a weight average molecular weight of from about 50,000 to about 700,000. It has been found that hydroxyethyl cellulose is the most hydrophilic suitable cellulose ether substrate, and therefore, can allow for greater modification than other suitable water-soluble cellulose ether substrates before water-insolubility is achieved. Accordingly, control of the modification process and control of the properties of the modified substrate can be more precise with hydroxyethyl cellulose substrates. Hydrophilicity of the most commonly used nonionic cellulose ethers ranges from hydroxyethyl to hydroxypropyl to hydroxypropylmethyl to methyl, with hydroxyethyl being the most hydrophilic and methyl being the least hydrophilic.

The long chain alkyl modifier can be attached to the cellulose ether substrate via an ether, ester, or urethane linkage. The ether linkage is preferred. The size and effect of the hydrocarbon chain of suitable modifiers effectively conceals any noticeable effect derived from functional groups other than alkyl halides which links the modifier to the substrate. In other words, if the long chain alkyl modifier is an epoxide containing an alphahydroxyalkyl radical, an isocyanate containing a urethane radical, or an acyl chloride containing an acyl radical, the effect of these functional groups are unnoticeable and the performance of the hydrophobically modified nonionic cellulose polymer is not significantly different from a polymer modified with an alkyl halide modifier.

Specific examples of preferred hydrophobically modified nonionic cellulose polymers include Natrosol Plus Grade 330, and Natrosol Plus CS Grade D-67, both commercially available from the Aqualon Company located in Wilmington, Del. Natrosol Plus Grade 330 is a hydrophobically modified hydroxyethylcellulose which has a weight average molecular weight of approximately 300,000 prior to modification; which has been substituted with from about 0.4% to about 0.8%, by weight, of an alkyl modifier having sixteen carbon atoms; and which has a hydroxyethyl molar substitution of from about 3.0 to about 3.7. Natrosol Plus CS Grade D-67 is a hydrophobically modified hydroxyethylcellulose which has a weight average molecular weight of approximately 700,000 prior to modification; which has been substituted with from about 0.50% to about 0.95%, by weight, of an alkyl modifier having sixteen carbon atoms; and which has a hydroxyethyl molar substitution of from about 2.3 to about 3.3.

Other cellulose polymers which can provide measurable viscosity increase to the residue are also suitable for use as an optional gelling agent herein. A specific example of other suitable cellulose polymers include a water-soluble hydrophobically modified cationic cellulose polymer commercially available as Quatrosoft from Amerchol.

Other Optional Materials

Other optional materials suitable for use in the aerosol hair styling compositions of the present invention include, but are not limited to, preservatives, surfactants, conditioning polymers, electrolytes, fatty alcohols, hair dyes, antidandruff actives, odor masking agents, pH adjusting agents, perfume oils, perfume solubilizing agents, sequestering agents, emollients, lubricants and penetrants such as various lanolin compounds, protein hydrolysates and other protein derivatives, sunscreens, volatile silicone fluids, and isoparrafins. The concentration of such optional ingredients generally ranges from zero to about 25%, more typically from about 0.05% to about 25%, even more typically from about 0.1% to about 15%, by weight of the composition.

Method of Manufacture

The aerosol hair styling compositions of the present invention may be prepared by any known or otherwise effective technique, suitable for providing an aerosol hair styling composition provided that the composition is formulated to contain the requisite hair styling agent defined herein.

Methods for preparing the aerosol hair styling compositions of the present invention include conventional formulation and mixing techniques. Suitable methods include combining the styling agent with the liquid carrier, and thoroughly mixing until the styling agent is homogenously dispersed and dissolved in the liquid carrier. Any remaining ingredients such as perfume, the optional styling polymer, and the optional preferred gelling agent, can then be added and dispersed into the mixture. The resultant liquid mixture is then packaged into a suitable container such as an aerosol dispenser, and the propellant is then added.

The aerosol hair styling composition of the present invention can be contained or dispensed in any known or otherwise effective aerosol container or delivery system. All such containers or delivery systems should be compatible with the essential and any selected optional ingredients of the hair styling composition of the present invention.

Alternatively, pressurized aerosol dispensers can be used where the propellant is separated from contact with the hair styling composition by use of specialized containers such as a two compartment can of the type sold under the tradename SEPRO from American National Can Corp.

The hair styling compositions of present invention can also be formulated as nonaerosol compositions. Methods for preparing nonaerosol hair styling compositions such as pomades include any known or otherwise effective manufacturing or formulation method for formulating such products.

Method Of Use

The hair styling compositions of the present invention are used to provide hairstyle/hold benefits without having to reapply the compositions for several days. An effective amount of the composition is either sprayed or applied onto dry hair before or after the hair is styled. As used herein "effective amount" means an amount sufficient to provide the hair hold and style performance desired according to the length and texture of the hair.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. All exemplified concentrations are weight-weight percents, unless otherwise specified.

Examples I–XII

The following Examples I–XII describe hair mousse compositions of the present invention. Each of the exemplified compositions are prepared by combining all of the listed components, except the propellant, and mixing the combination for 40 minutes. The resultant liquid mixture is then filled into an aerosol container, and the propellant is added. Alternatively, for Examples VII and VIII, the dimethicone can be pre-mixed with the propellant so that the mixture is pressure filled into the aerosol container. Each of the exemplified hair mousse compositions provides improved dry hair restyle performance without the need to reapply the composition or add any other additional styling aids.

| Hair Mousse Compositions | | | | |
|---|---|---|---|---|
| Component: | Example I | Example II | Example III | Example IV |
| PEG-8[1] | 20.0 | — | — | — |
| PEG-12[2] | — | 15.0 | — | — |
| PEG-20[3] | — | — | 20.0 | 20.0 |
| Ethanol (Denatured) | 10.0 | 5.0 | 5.0 | 5.0 |
| Polydimethylsiloxane (350 cs)[4] | — | — | 5.0 | 5.0 |
| Silicone-Polyether Copolymer[5] | 5.0 | — | — | — |
| Sodium Cocoyl Isethionate | — | 0.50 | — | — |
| Benzyl Alcohol | 0.50 | 0.50 | 0.50 | — |
| Undeceth-9[6] | — | 0.50 | 0.50 | — |
| Cocamide DEA | 0.50 | — | — | 0.50 |
| Lauramide DEA | — | — | — | 0.50 |
| Cocamidopropyl Betaine | 0.50 | — | — | — |
| DMDM Hydantoin | — | — | — | 0.50 |
| Phenoxyethanol | 0.30 | 0.30 | 0.30 | 0.30 |
| Perfume | 0.15 | 0.15 | 0.15 | 0.15 |
| Disodium EDTA | — | 0.12 | 0.12 | 0.12 |
| Propellant Aeron A-70[7] | 7.0 | 10.0 | — | — |
| Propellant Aeron A-46[7] | — | — | 7.0 | 10.0 |
| Distilled Water | qs | qs | qs | qs |

[1]Carbowax 400 available from Union Carbide
[2]Carbowax 600 available from Union Carbide
[3]Carbowax 900 available from Union Carbide
[4]SF96-60,000 available from General Electric
[5]Silwet L-77 available from Witco
[6]Neodol 1-9 available from Shell
[7]Propane/Isobutane mixture available from Diversified CPC

| Hair Mousse Compositions | | | | |
|---|---|---|---|---|
| Component: | Example V | Example VI | Example VII | Example VIII |
| PEG-8[1] | 10.0 | — | — | — |
| PEG-12[2] | — | 12.0 | — | 6.00 |
| PEG-20[3] | — | — | 12.0 | — |
| Ethanol (Denatured) | 10.0 | — | 5.0 | 5.0 |
| Silicone emulsion[4] | 10.0 | 8.0 | — | — |
| Polydimethylsiloxane (350 cs)[5] | — | — | 3.0 | 1.5 |
| Silicone-Polyether Copolymer[6] | 5.0 | — | — | — |
| Sodium Cocoyl Isethionate | — | 0.50 | — | — |
| Benzyl Alcohol | 0.50 | 0.50 | 0.50 | 0.50 |
| Undeceth-9[7] | — | 0.50 | 0.50 | — |
| Cocamide DEA | 0.50 | — | — | 0.50 |
| Lauramide DEA | — | — | — | 0.50 |
| Cocamidopropyl Betaine | 0.50 | — | — | — |
| DMDM Hydantoin | — | — | — | 0.50 |
| Phenoxyethanol | 0.30 | 0.30 | 0.30 | 0.30 |
| Perfume | 0.15 | 0.15 | 0.15 | 0.15 |
| Disodium EDTA | — | 0.12 | 0.12 | 0.12 |
| Propellant Aeron A-70[8] | 7.0 | 10.0 | — | — |
| Propellant Aeron A-46[8] | — | — | 7.0 | 10.0 |
| Distilled Water | qs | qs | qs | qs |

[1]Carbowax 400 available from Union Carbide
[2]Carbowax 600 available from Union Carbide
[3]Carbowax 900 available from Union Carbide -continued Hair Mousse Compositions

| Component: | Example V | Example VI | Example VII | Example VIII |
|---|---|---|---|---|

[4]50% dimethicone (100,000 cps) emulsion available from Toray Silicones
[5]SF96-60,000 available from General Electric
[6]Silwet L-77 available from Witco
[7]Neodol 1-9 available from Shell
[8]Propane/Isobutane mixture available from Diversified CPC Hair Mousse Compositions

| Component: | Example IX | Example X | Example XI | Example XII |
|---|---|---|---|---|
| PEG-6[1] | 5.0 | — | — | — |
| PEG-8[2] | — | 12.0 | — | 15.0 |
| PEG-18 | — | — | 5.0 | — |
| PEG-32[3] | 10.0 | — | — | — |
| Glydant | 0.37 | — | 0.37 | — |
| Triglycerin | — | — | 5.0 | — |
| Silicone | 12.0[4] | 7.0[3] | 5.0[4] | 10.0[4] |
| Ditallowdimonium Chloride | 0.50 | — | — | — |
| Benzyl Alcohol | — | 0.50 | — | 0.50 |
| Undeceth-9[6] | 0.50 | — | — | — |
| Phenoxyethanol | — | 0.30 | — | 0.30 |
| Steartrimonium Chloride | — | 0.10 | 0.30 | — |
| PEG-60 Castor Oil | — | — | 0.20 | — |
| Perfume | 0.15 | — | — | 0.15 |
| Disodium EDTA | — | — | — | 0.09 |
| Propellant Aeron A-70[7] | 10.0 | — | — | — |
| Propellant Aeron A-46[7] | — | 10.0 | 10.0 | 7.0 |
| Distilled Water | qs | qs | qs | qs |

[1]Carbowax 300 available from Union Carbide
[2]Carbowax 400 available from Union Carbide
[3]Carbowax 1450 available from Union Carbide
[4]Dimethicone oil (60,000 cps) available form General Electric
[5]50% dimethicone (100,000 cps) emulsion available from Toray Silicones
[6]Neodol 1-9 available from Shell
[7]Propane/Isobutane mixture available from Diversified CPC

Examples XIII–XXI

The following Examples XIII–XXI describe hair mousse compositions of the present invention. Each of the exemplified compositions are prepared by adding the styling agent to water and mixing for one hour until the styling agent is dissolved. The remaining ingredients, except the propellant, are then added and the resulting solution is stirred. The composition is then packaged into an aerosol container, and the propellant is added. Each of the exemplified hair mousse compositions provides improved dry hair restyle performance without the need to reapply the composition or add any other additional styling aids.

Hair Mousse Compositions

| Component: | Example XIII | Example XIV | Example XV | Example XVI |
|---|---|---|---|---|
| PEG-8[1] | 18.0 | — | 15.0 | 10.0 |
| Kytamer L[2] | — | 1.00 | — | — |
| EMA 8[3] | 0.72 | — | — | — |
| Silicone | 4.5[4] | 7.0[5] | 8.00[4] | 7.00[5] |
| Laponite XLG[6] | — | — | 1.00 | — |
| Hexaglycerol[7] | — | — | — | 5.0 |
| Carbopol 934[8] | — | — | 0.30 | 0.15 |
| Permulan TR-1[9] | — | — | 0.10 | — |
| Benzyl Alcohol | 0.45 | 0.45 | 0.50 | 0.50 |

-continued

Hair Mousse Compositions

| Component: | Example XIII | Example XIV | Example XV | Example XVI |
|---|---|---|---|---|
| Phenoxyethanol | 0.27 | 0.27 | 0.30 | 0.30 |
| Undeceth-9[10] | 0.27 | 0.27 | 0.30 | 0.30 |
| Sodium Cocoyl Isethionate | 0.18 | — | — | 0.20 |
| Disodium EDTA | 0.11 | — | 0.12 | 0.12 |
| Perfume | 0.13 | 0.11 | 0.15 | 0.15 |
| Aminomethylpropanol | 0.35 | — | 0.30 | 0.10 |
| Propellant Aeron A-46[11] | 10.0 | — | 7.50 | 10.0 |
| Propellant Aeron A-70[11] | — | 10.0 | — | — |
| Distilled Water | qs | qs | qs | qs |

[1]Carbowax 400 available from Union Carbide
[2]neutralized Chitosan available from Amerchol
[3]unneutralized ethylene/maleic anhydride copolymer available from Monsanto
[4]10,000 cps silicone oil available from GE
[5]10,000 cps dimethicone emulsion available from General electric
[6]styling clay available from Southern Clay Products
[7]available from Solvay Interox, Inc.
[8]crosslinked carboxylic acid homopolymer available from B.F. Goodrich
[9]crosslinked carboxylic acid copolymer available from B.F. Goodrich
[10]Neodol 1-9 available from Shell
[11]Propane/isobutane mixture available from Diversified CPC

Hair Mousse Compositions

| Component: | Example XVII | Example XVIII | Example XIX | Example XX | Example XXI |
|---|---|---|---|---|---|
| PEG-8[1] | 5.0 | — | — | — | 10.0 |
| PEG-12[2] | — | 5.00 | — | 5.00 | — |
| PEG-20[3] | — | — | 15.0 | — | — |
| Ucare JR-400[4] | — | — | 1.00 | 3.00 | — |
| Celquat L-200[5] | 0.75 | 0.50 | 1.00 | — | 1.00 |
| Permulan TR-1[6] | — | — | 0.50 | — | — |
| Benzyl Alcohol | 0.50 | 0.50 | — | — | — |
| Phenoxyethanol | 0.30 | 0.30 | — | — | — |
| Undeceth-9[7] | 0.30 | 0.15 | 0.30 | — | — |
| Isosteareth-20 | — | 0.15 | 0.20 | 0.40 | 0.35 |
| Disodium EDTA | 0.12 | 0.12 | — | — | — |
| Natrosol 250 VR[8] | 1.25 | 1.50 | — | — | — |
| Perfume | 0.15 | 0.15 | 0.15 | 0.12 | 0.25 |
| Triethanolamine | — | — | 0.40 | — | — |
| Kathon CG[9] | — | — | 0.04 | 0.04 | 0.04 |
| Propellant Aeron A-46[10] | — | — | 10.0 | — | — |
| Propellant Aeron A-70[10] | 10.0 | 10.0 | — | — | — |
| Distilled Water | qs | qs | qs | qs | qs |

[1]Carbowax 400 available from Union Carbide
[2]Carbowax 600 available from Union Carbide
[3]Carbowax 900 available from Union Carbide
[4]anionic polysaccharide polymer available from Aqualon
[5]cationic polysaccharide copolymer available from National Starch
[6]crosslinked carboxylic acid copolymer available from B.F. Goodrich
[7]Neodol 1-9 available from Shell
[8]hydroxyethylcellulose available from Aqualon
[9]preservative available from Rohm & Haas
[10]propane/isobutane mixture available from Diversified CPC

Examples XXII–XXIII

The hair styling compositions of the present invention include the pomade embodiment described below. The pomade is formulated by dispersing the Carbopol 934 into a solution containing all the listed ingredients except the aminomethylpropanol, and thoroughly mixing for 30 minutes. The aminomethylpropanol is then slowly added to and thoroughly mixed in the resulting solution for 10 minutes. The resultant composition may be packaged into any well known container for packaging such pomade compositions. The exemplified pomade composition of the present invention provides improved dry hair restyle performance without the need to reapply the composition or add any other additional styling aids.

Pomade Compositions

| Component | Example XXII | Example XXIII |
|---|---|---|
| PEG-14 | 80.00 | 48.00 |
| Carbopol 934[1] | 1.00 | 1.00 |
| Aminomethylpropanol | 0.30 | 0.30 |
| Silicone Emulsion[2] | — | 30.00 |
| Polysorbate 80 | 0.40 | 0.40 |
| Glydant | — | 0.37 |
| Fragrance | 0.20 | 0.20 |
| Distilled Water | Q.S. | Q.S. |

[1]crosslinked carboxylic acid homopolymer available from B.F. Goodrich
[2]50% dimethicone emulsion (100,000 cps) available from Toray Silicones

Examples XXIV–XXV

The hair styling compositions of the present invention include the spray-on-gel embodiments described below. The spray-on gels are formulated by combining all the listed ingredients, except the propellant and mixing for 10 minutes. The compositions are then packaged into an aerosol container and the propellant is added. These spray-on gel compositions provide improved dry hair restyle performance without the need to reapply the composition or add any other additional styling aids.

Spray-on-gel Compositions

| Component | Example XXIV | Example XXV |
|---|---|---|
| PEG-20[1] | 8.00 | 8.00 |
| Silicone Emulsion[2] | — | 7.00 |
| Fragrance | 0.10 | 0.10 |
| Isobutane | 5.00 | — |
| Dimethyl Ether | 25.00 | 25.00 |
| Ethanol, Denatured | 20.00 | 10.00 |
| Distilled Water | Q.S. | Q.S. |

[1]Carbowax 900 available from Union Carbide
[2]Dimethicone (60,000 cps) emulsion available from General Electric Corporation

Examples XXVI–XXVII

The following Examples describe pump hairspray compositions of the present invention. Example XXVI is prepared by adding the Pemulen to water and mixing for one half hour until dispersed. The remaining ingredients, except for TEA, are added and the resulting solution is stirred. The TEA is then added and mixed for one half hour. Example XXVII is prepared by combining all ingredients and mixing for 15 minutes. Each of these hairspray compositions provides improved hair volume and hair hold.

Pump Hairspray Compositions

| Component | Example XXVI | Example XXVII |
|---|---|---|
| PEG-8[1] | 16.00 | — |
| PEG-12[2] | — | 10.00 |
| Silicone Emulsion[3] | 10.00 | 6.0 |
| Pemulen TR-1 | 0.20 | — |
| Benzyl Alcohol | 0.45 | 0.45 |

[1]Carbowax 400 available from Union Carbide
[2]Carbowax 600 available from union Carbide
[3]50% dimethicone (100,000 cps) emulsion available from Toray Silicones

| Component | Example XXVIII | Example XXIX |
|---|---|---|
| Water | QS | QS |
| Ethanol | 20.000 | 20.000 |
| PEG-8[1] | — | 8.000 |
| PEG-12[2] | 5.000 | — |
| Nonionic cellulosic derivative[3] | 1.250 | 1.500 |
| Cationic polysaccharide polymer[4] | .750 | 0.500 |
| Isosteareth-20[5] | .650 | .650 |
| Benzyl Alcohol | .500 | .500 |
| Phenoxyethanol | .300 | .300 |
| Methyl Paraben | .200 | .200 |
| Policher | .150 | .150 |
| Dosodium EDTA | .120 | .120 |

[1]Carbowax 400 available from Union Carbide
[2]Carbowax 600 available from union Carbide
[3]Natrosol 250 JR available from Aqualon
[4]Celquat L-200 available from National Starch
[5]Arosurf 66-E-20

The Celquat and Natrosol are dispersed slowly into a tank containing all the water. It is mixed with vigorous agitation for about an hour. At that time the remaining ingredients are added in the order listed and the batch is mixed vigorously an additional half hour. The batch is then poured into pump spray bottles.

What is claimed is:

1. An aerosol hair styling composition comprising:
   (a) from about 5% to about 90% by weight of a water-soluble polyalkylene glycol that is substantially free of polyalkylene glyceryl ethers and that has a number average molecular weight of from about 190 to about 1500 and from about 12 to about 35 repeating alkylene oxide radicals wherein each of the repeating alkylene oxide radicals has from 2 to 6 carbon atoms;
   (b) from about 1% to about 90% by weight of a liquid carrier; and
   (c) from about 5% to about 40% by weight of a propellant.

2. The composition of claim 1 wherein the composition comprises from about 7.5% to about 50% by weight of the water-soluble polyalkylene glycol.

3. The composition of claim 2 wherein the water-soluble polyalkylene glycol is selected from the group consisting of ethoxy polyethylene/polypropylene glycol copolymers, methoxy polyethylene/polypropylene glycol copolymers, propoxy polyethylene/polypropylene glycol copolymers, butoxy polyethylene/polypropylene glycol copolymers, pentoxy polyethylene/polypropylene glycol copolymers, triglycerin, hexaglycerin, PEG-4, PEG-6, PEG-5, PEG-6, PEG-8, PEG-12, PEG-14, PEG-18, PEG-20, PEG-32, and mixtures thereof.

4. The composition of claim 3 wherein the liquid carrier is selected from the group consisting of water, $C_1$–$C_6$ alkanols, carbitol, acetone, and mixtures thereof.

5. The composition of claim 4 wherein the composition further comprises a polysaccharide styling polymer.

6. The composition of claim 4 which further comprises a blend of a cationic polysaccharide styling polymer and a nonionic styling polymer, wherein the cationic polymer comprises from about 15% to about 85% by weight of the blend.

7. The composition of claim 2 wherein the composition further comprises a gelling agent, wherein the gelling agent is a water-soluble polymer selected from the group consisting of crosslinked ethylene/maleic anhydride copolymers, crosslinked carboxylic acid polymers, hydrophobically modified nonionic cellulose polymers, and mixtures thereof.

8. A hair mousse composition comprising:
   (a) from about 5% to about 25% by weight of a polyalkylene glycol that is substantially free of polyalkylene glyceryl ethers and that has a number average molecular weight of from about 190 to about 1500 and from about 12 to about 35 repeating alkylene oxide radicals wherein each of the repeating alkylene oxide radicals has from 2 to 6 carbon atoms;
   (b) from about 10% to about 90% by weight of water; and
   (c) from about 5% to about 40% by weight of a propellant.

9. The composition of claim 8 wherein the polyalkylene glycol is selected from the group consisting of ethoxy polyethylene/polypropylene glycol copolymers, methoxy polyethylene/polypropylene glycol copolymers, propoxy polyethylene/polypropylene glycol copolymers, butoxy polyethylene/polypropylene glycol copolymers, pentoxy polyethylene/polypropylene glycol copolymers, triglycerin, hexaglycerin, PEG-4, PEG-6, PEG-5, PEG-6, PEG-8, PEG-12, PEG-14, PEG-18, PEG-20, PEG-32, and mixtures thereof.

10. The composition of claim 9 wherein the composition further comprises an organic solvent selected from the group consisting of $C_1$–$C_6$ alkanols, carbitol, acetone, and mixtures thereof.

11. The composition of claim 9 wherein the composition further comprises a polysaccharide styling polymer.

12. The composition of claim 11 wherein the polysaccharide styling polymer is selected from the group consisting of glucosamine polysaccharide derivatives, cationic polysaccharides, anionic polysaccharides, and mixtures thereof.

13. The composition of claim 12 wherein the composition further comprises a gelling agent, wherein the gelling agent is a water-soluble polymer selected from the group consisting of crosslinked ethylene/maleic anhydride copolymers, crosslinked carboxylic acid polymers, hydrophobically modified nonionic cellulose polymers, and mixtures thereof.

14. A method of making an improved hair mousse composition wherein the method comprises the steps of:
   (a) preparing a reformable weld formulation comprising:
       (i) from about 5% to about 25% by weight of a polyalkylene glycol having a number average molecular weight of from about 190 to about 1500 and from about 12 to about 35 repeating alkylene oxide radicals wherein each of the repeating alkylene oxide radicals has from 2 to 6 carbon atoms;
       (ii) from about 40% to about 90% by weight of water; and
       (iii) from about 5% to about 10% by weight of an organic solvent; and
   (b) packaging the reformable weld formulation in an aerosol container, wherein the aerosol container comprises a propellant, and wherein the reformable weld formulation is substantially free of polyalkylene glyceryl ethers.

15. A hair styling composition comprising:
   (a) from about 65% to about 99% by weight of a polyalkylene glycol that is substantially free of polyalkylene glyceryl ethers and that has a number average molecular weight of from about 190 to about 1500 and from about 12 to about 35 repeating alkylene oxide radicals wherein each of the repeating alkylene oxide radicals has from 2 to 6 carbon atoms; and
   (b) from about 1% to about 30% by weight of a liquid carrier.

16. The composition of claim 15 wherein the polyalkylene glycol is selected from the group consisting of ethoxy polyethylene/polypropylene glycol copolymers, methoxy polyethylene/polypropylene glycol copolymers, propoxy polyethylene/polypropylene glycol copolymers, butoxy polyethylene/polypropylene glycol copolymers, pentoxy polyethylene/polypropylene glycol copolymers, triglycerin, hexaglycerin, PEG-4, PEG-6, PEG-5, PEG-6, PEG-8, PEG-12, PEG-14, PEG-1 8, PEG-20, PEG-32, and mixtures thereof.

17. A hair styling composition comprising:
   (a) from about 5% to about 80% by weight of a polyalkylene glycol that is substantially free of polyalkylene glyceryl ethers and that has a number average molecular weight of from about 190 to about 1500 and from about 12 to about 35 repeating alkylene oxide radicals wherein each of the repeating alkylene oxide radicals has from 2 to 6 carbon atoms; and
   (b) from about 1% to about 30% by weight of a liquid carrier,
   (c) a blend of cationic polysaccharide styling polymer and a nonionic styling polymer,
   wherein the cationic polysaccharide polymer comprises from about 15% to about 85% by weight of the blend.

18. A method for styling dry hair, which method comprises applying an effective amount of the composition of claim 1 to the hair.

19. A method for styling dry hair, which method comprises applying an effective amount of the composition of claim 15 to the hair.

20. A hair styling composition comprising:
   (a) from about 5% to about 90% by weight of a water-soluble polyalkylene glycol that has a number average molecular weight of from about 190 to about 1500 and from about 12 to about 35 repeating alkylene oxide radicals wherein each of the repeating alkylene oxide radicals has from 2 to 6 carbon atoms;
   (b) from about 1% to about 90% by weight of a liquid carrier; and
   (c) from about 1.5% to about 60% by weight of a silicone or silicone derivative with a molecular weight greater than 40,000 daltons, wherein the ratio of the water-soluble polyalkylene glycol to the silicone or silicone derivative ranges from about 4:1 to about 1:4.

21. The composition of claim 20 wherein the composition comprises from about 7.5% to about 50% by weight of the water-soluble polyalkylene glycol.

22. The composition of claim 21 wherein the water-soluble polyalkylene glycol is selected from the group consisting of ethoxy polyethylene/polypropylene glycol copolymers, methoxy polyethylene/polypropylene glycol copolymers, propoxy polyethylene/polypropylene glycol copolymers, butoxy polyethylene/polypropylene glycol copolymers, pentoxy polyethylene/polypropylene glycol copolymers, triglycerin, hexaglycerin, PEG-4, PEG-6, PEG-5, PEG-6, PEG-8, PEG-12, PEG-14, PEG-18, PEG-20, PEG-32, and mixtures thereof.

23. The composition of claim 22 wherein the liquid carrier is selected from the group consisting of water, $C_1$–$C_6$ alkanols, carbitol, acetone, and mixtures thereof.

24. The composition of claim 23 wherein the composition further comprises a polysaccharide styling polymer.

25. The composition of claim 24 which further comprises a blend of a cationic polysaccharide styling polymer and a nonionic styling polymer, wherein the cationic polymer comprises from about 15% to about 85% by weight of the blend.

26. The composition of claim 25 wherein the composition further comprises a gelling agent, wherein the gelling agent is a water-soluble polymer selected from the group consisting of crosslinked ethylene/maleic anhydride copolymers, crosslinked carboxylic acid polymers, hydrophobically modified nonionic cellulose polymers, and mixtures thereof.

27. The composition of claim 20 which further comprises a propellant.

28. The composition of claim 25 which further comprises a propellant.

29. A method of making a hair mousse composition wherein the method comprises the steps of:
   (a) preparing a reformable weld formulation comprising:
      (i) from about 9% to about 25% by weight of a polyalkylene glycol having a number average molecular weight of from about 190 to about 1500 and from about 12 to about 35 repeating alkylene oxide radicals wherein each of the repeating alkylene oxide radicals has from 2 to 6 carbon atoms;
      (ii) from about 40% to about 90% by weight of water; and
      (iii) from about 1.5% to about 60% by weight of a silicone or silicone derivative having a molecular weight greater than 40,000 daltons, wherein the ratio of the polyalkylene glycol to the silicone or silicone derivative ranges from about 4:1 to about 1:4; and
   (b) packaging the reformable weld formulation in an aerosol container, wherein the aerosol container comprises from about 5% to about 40%, by weight of the composition, of a propellant.

30. A method for styling dry hair, which method comprises applying an effective amount of the composition of claim 20 to the hair.

* * * * *

UNITED STATES PATENT AND TRADEMARK OFFICE
CERTIFICATE OF CORRECTION

PATENT NO. : 6,635,240 B1
DATED : October 21, 2003
INVENTOR(S) : Raymond Edward Bolich, Jr. et al.

It is certified that error appears in the above-identified patent and that said Letters Patent is hereby corrected as shown below:

<u>Title page,</u>
Item [63], delete "now abandoned".

Signed and Sealed this

Twenty-seventh Day of January, 2004

JON W. DUDAS
*Acting Director of the United States Patent and Trademark Office*